(12) United States Patent
Gaines et al.

(10) Patent No.: US 10,029,841 B2
(45) Date of Patent: *Jul. 24, 2018

(54) DAMAGE INDICATING PACKAGING

(71) Applicant: Baby Blue Brand Corp., Bala Cynwyd, PA (US)

(72) Inventors: L. Kris Gaines, Portsmouth, VA (US); Veonous M. Jacques, Philadelphia, PA (US); Auguste Jacques, Philadelphia, PA (US); David A. Gaines, Portsmouth, VA (US); Crystal G. Morrison, Pittsburgh, PA (US)

(73) Assignee: Baby Blue Brand, Bala Cynwyd, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/939,989

(22) Filed: Nov. 12, 2015

(65) Prior Publication Data

US 2016/0137381 A1    May 19, 2016

Related U.S. Application Data

(63) Continuation-in-part of application No. 14/272,156, filed on May 7, 2014.

(60) Provisional application No. 61/820,315, filed on May 7, 2013, provisional application No. 61/971,187, filed on Mar. 27, 2014, provisional application No. 62/078,819, filed on Nov. 12, 2014.

(51) Int. Cl.
| | |
|---|---|
| *A61F 6/00* | (2006.01) |
| *B65D 85/16* | (2006.01) |
| *B32B 33/00* | (2006.01) |
| *A45C 11/00* | (2006.01) |
| *B65D 79/02* | (2006.01) |
| *B65D 75/04* | (2006.01) |

(52) U.S. Cl.
CPC .............. *B65D 79/02* (2013.01); *A61F 6/005* (2013.01); *B65D 75/04* (2013.01); *B65D 2101/0084* (2013.01)

(58) Field of Classification Search
CPC .......... B65D 2101/0084; B65D 55/026; B65D 2101/00; A45C 2011/007; A61F 6/005; Y10S 428/916; G01N 31/223; A61L 2/28; G09F 3/03
USPC ............ 383/5; 229/102; 206/459.1; 215/365
See application file for complete search history.

(56) References Cited

U.S. PATENT DOCUMENTS

| | | | | |
|---|---|---|---|---|
| 1,818,726 | A | * | 8/1931 | Lowe ........................ B44F 1/10 383/5 |
| 2,998,306 | A | * | 8/1961 | Huyck ................. G01N 31/221 116/DIG. 14 |
| 3,221,428 | A | * | 12/1965 | Fischler ................. B42D 25/00 116/200 |

(Continued)

*Primary Examiner* — J. Gregory Pickett
*Assistant Examiner* — Gideon Weinerth
(74) *Attorney, Agent, or Firm* — Alan G. Towner, Esq.; Leech Tisham Fuscaldo & Lampl

(57) ABSTRACT

Damage indicating packaging is disclosed. A damage indicating material may be applied between inner and outer wrapper layers. When the damage indicating material is exposed to oxygen, excessive heat and/or excessive pressure, the material changes in appearance to thereby alert the user that the package may be compromised. The damage indicating material may include an anti-counterfeiting taggant material. Active and intelligent tamper-evident packaging is thus provided.

17 Claims, 11 Drawing Sheets

(56) References Cited

U.S. PATENT DOCUMENTS

| | | | | |
|---|---|---|---|---|
| 3,633,216 A * | 1/1972 | Schonholtz | A61B 42/10 | 2/168 |
| 3,899,295 A * | 8/1975 | Halpern | A61L 2/28 | 101/491 |
| 4,505,399 A * | 3/1985 | Weiner | B65D 55/026 | 215/203 |
| 4,516,679 A * | 5/1985 | Simpson | B65D 75/52 | 206/459.1 |
| 4,526,752 A * | 7/1985 | Perlman | B65D 55/026 | 116/207 |
| 4,843,014 A * | 6/1989 | Cukier | A41D 19/0058 | 128/846 |
| 4,877,143 A * | 10/1989 | Travisano | B65D 55/066 | 116/270 |
| 4,905,851 A * | 3/1990 | Thompson | B65D 55/026 | 215/203 |
| 4,910,803 A * | 3/1990 | Cukier | A41D 19/0058 | 128/844 |
| 4,919,966 A * | 4/1990 | Shlenker | A61B 42/10 | 116/214 |
| 4,931,327 A * | 6/1990 | Liu | B32B 27/20 | 206/807 |
| 4,986,429 A * | 1/1991 | Singleton, Jr. | B65D 41/62 | 206/459.1 |
| 5,005,695 A * | 4/1991 | Tennefos | A61F 6/005 | 206/69 |
| 5,020,831 A * | 6/1991 | Benardelli | G09F 3/0292 | 283/101 |
| 5,024,852 A * | 6/1991 | Busnel | A61F 6/04 | 427/2.3 |
| 5,062,928 A * | 11/1991 | Smith | C25D 11/04 | 205/122 |
| 5,234,732 A * | 8/1993 | Versic | B32B 27/08 | 206/459.1 |
| 5,411,034 A * | 5/1995 | Beck | A61F 6/04 | 128/844 |
| 5,472,668 A * | 12/1995 | Mills | G01N 21/783 | 422/425 |
| 5,480,611 A * | 1/1996 | Mills | G01N 31/223 | 128/200.26 |
| 5,524,294 A * | 6/1996 | Richardson | A41D 19/0058 | 2/161.7 |
| 5,549,924 A * | 8/1996 | Shlenker | A01N 25/10 | 128/844 |
| 5,581,978 A * | 12/1996 | Hekal | B65D 55/026 | 53/411 |
| 5,620,256 A * | 4/1997 | Makrauer | B65D 33/1691 | 383/5 |
| 5,650,329 A * | 7/1997 | Warner | G01N 31/221 | 422/414 |
| 5,679,399 A * | 10/1997 | Shlenker | A61B 42/10 | 128/844 |
| 5,719,828 A * | 2/1998 | Haas | G04F 1/00 | 116/200 |
| 5,839,592 A * | 11/1998 | Hayes | B32B 27/08 | 215/230 |
| 5,849,594 A * | 12/1998 | Balderson | G01N 31/223 | 128/205.28 |
| 5,882,116 A * | 3/1999 | Backus | B65D 27/30 | 206/807 |
| 5,965,276 A * | 10/1999 | Shlenker | A01N 25/10 | 128/837 |
| 6,048,098 A * | 4/2000 | Vetter | B65D 33/34 | 383/5 |
| 6,149,203 A * | 11/2000 | Hanlon | G09F 3/0292 | 283/101 |
| 6,175,962 B1 * | 1/2001 | Michelson | A41D 19/0058 | 128/918 |
| 6,264,033 B1 * | 7/2001 | Kannabiran | B65D 33/34 | 206/459.1 |
| 6,596,354 B1 * | 7/2003 | Longdon | B65D 55/026 | 206/807 |
| 6,767,509 B1 * | 7/2004 | Griesbach | A61L 2/20 | 422/28 |
| 6,929,118 B1 * | 8/2005 | Izz | A61F 6/005 | 206/69 |
| 7,294,379 B2 * | 11/2007 | Ko | G01K 3/04 | 368/327 |
| 8,114,673 B2 * | 2/2012 | Mills | G01J 1/429 | 422/402 |
| 8,158,230 B2 * | 4/2012 | Culbertson | B32B 7/06 | 283/72 |
| 8,584,836 B2 * | 11/2013 | De Waleffe | B65D 75/5838 | 206/69 |
| 8,663,998 B2 * | 3/2014 | Heacock | C09K 9/02 | 252/408.1 |
| 9,248,045 B2 * | 2/2016 | Lee | A61F 6/005 | |
| 9,579,532 B2 * | 2/2017 | Hassan | A62D 5/00 | |
| 9,626,882 B2 * | 4/2017 | Dodrill | G09F 3/0341 | |
| 9,650,194 B2 * | 5/2017 | Hetherton | B65D 75/5894 | |
| 2003/0127846 A1 * | 7/2003 | Laurie | B41M 3/142 | 283/72 |
| 2005/0036716 A1 * | 2/2005 | Geyer | B65D 33/18 | 383/5 |
| 2005/0258129 A1 * | 11/2005 | Model | B65D 39/0011 | 215/230 |
| 2006/0026737 A1 * | 2/2006 | Chen | A61B 42/10 | 2/161.7 |
| 2006/0108405 A1 * | 5/2006 | Sanchez | B65D 27/14 | 229/80 |
| 2006/0234014 A1 * | 10/2006 | Liu | B65D 33/34 | 428/195.1 |
| 2008/0210580 A1 * | 9/2008 | Harrison | C10M 169/04 | 206/69 |
| 2009/0041083 A1 * | 2/2009 | McParland | B65D 51/24 | 374/162 |
| 2010/0278454 A1 * | 11/2010 | Huffer | B65D 75/5838 | 383/5 |
| 2011/0041856 A1 * | 2/2011 | Mistler | A61F 6/04 | 128/844 |
| 2011/0132788 A1 * | 6/2011 | Middlesworth | B65D 71/0092 | 206/459.5 |
| 2011/0268371 A1 * | 11/2011 | Kristal | B29C 59/02 | 383/5 |
| 2011/0287553 A1 * | 11/2011 | Hassan | B32B 33/00 | 436/164 |
| 2011/0308984 A1 * | 12/2011 | Hennek | A45C 1/02 | 206/459.1 |
| 2012/0142527 A1 * | 6/2012 | Smyth | G01N 31/225 | 503/201 |
| 2012/0165336 A1 * | 6/2012 | Steiner | A61J 1/035 | 514/249 |
| 2012/0222974 A1 * | 9/2012 | De Waleffe | B65D 75/5838 | 206/69 |
| 2012/0276647 A1 * | 11/2012 | Mills | G01N 21/78 | 436/113 |
| 2013/0130399 A1 * | 5/2013 | Mills | G01N 21/783 | 436/133 |
| 2013/0269592 A1 * | 10/2013 | Heacock | G01N 31/229 | 116/206 |
| 2014/0003743 A1 * | 1/2014 | Luffman | B65D 33/34 | 383/5 |
| 2014/0251859 A1 * | 9/2014 | Weikart | A61J 1/00 | 206/524.9 |
| 2014/0262898 A1 * | 9/2014 | Anderson | B65D 85/00 | 206/459.1 |
| 2015/0255009 A1 * | 9/2015 | Akhter | G09F 3/0292 | 206/459.1 |
| 2016/0180747 A1 * | 6/2016 | Pietarinen | G09F 3/0292 | 206/438 |

* cited by examiner

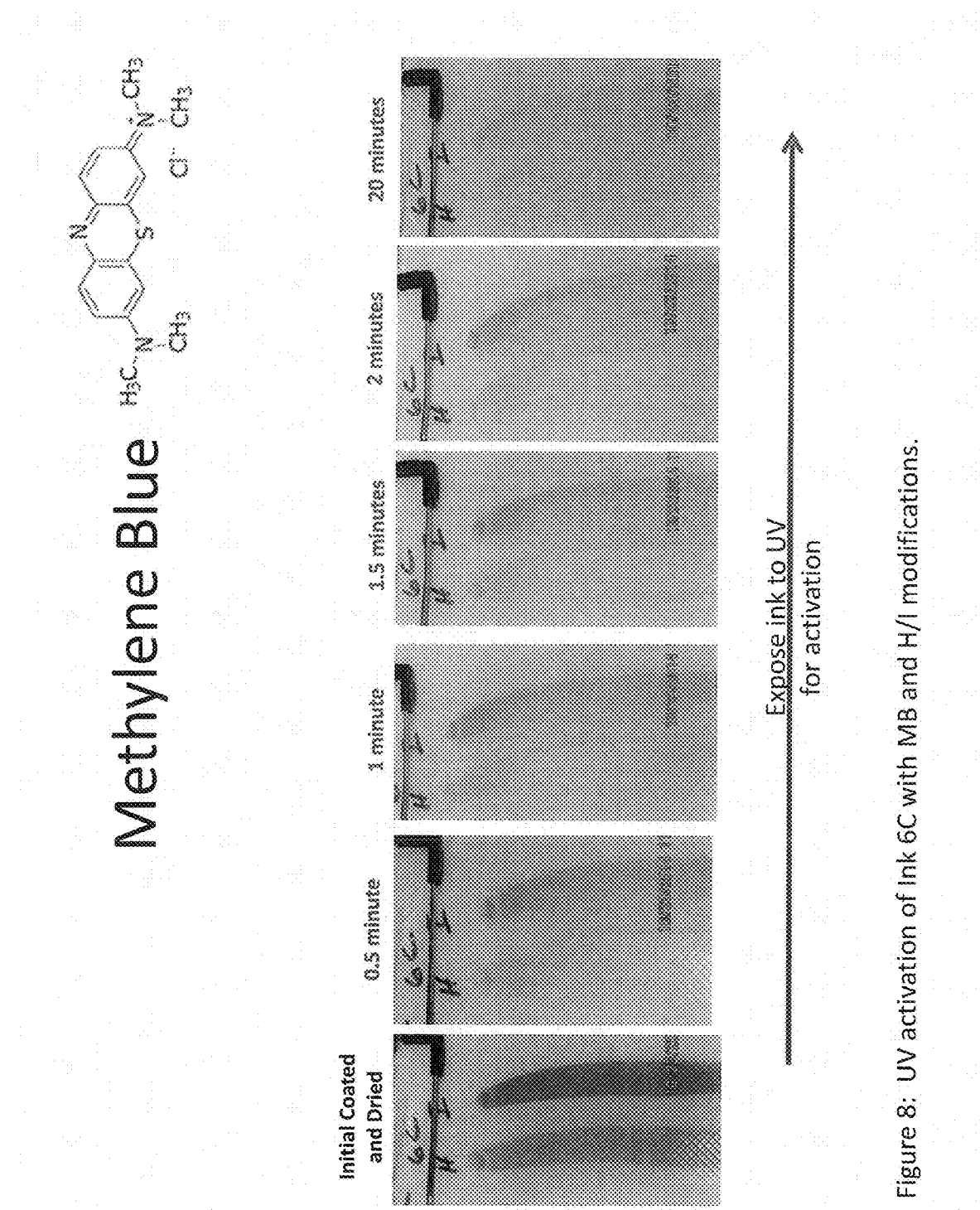
Figure 8: UV activation of Ink 6C with MB and H/I modifications.

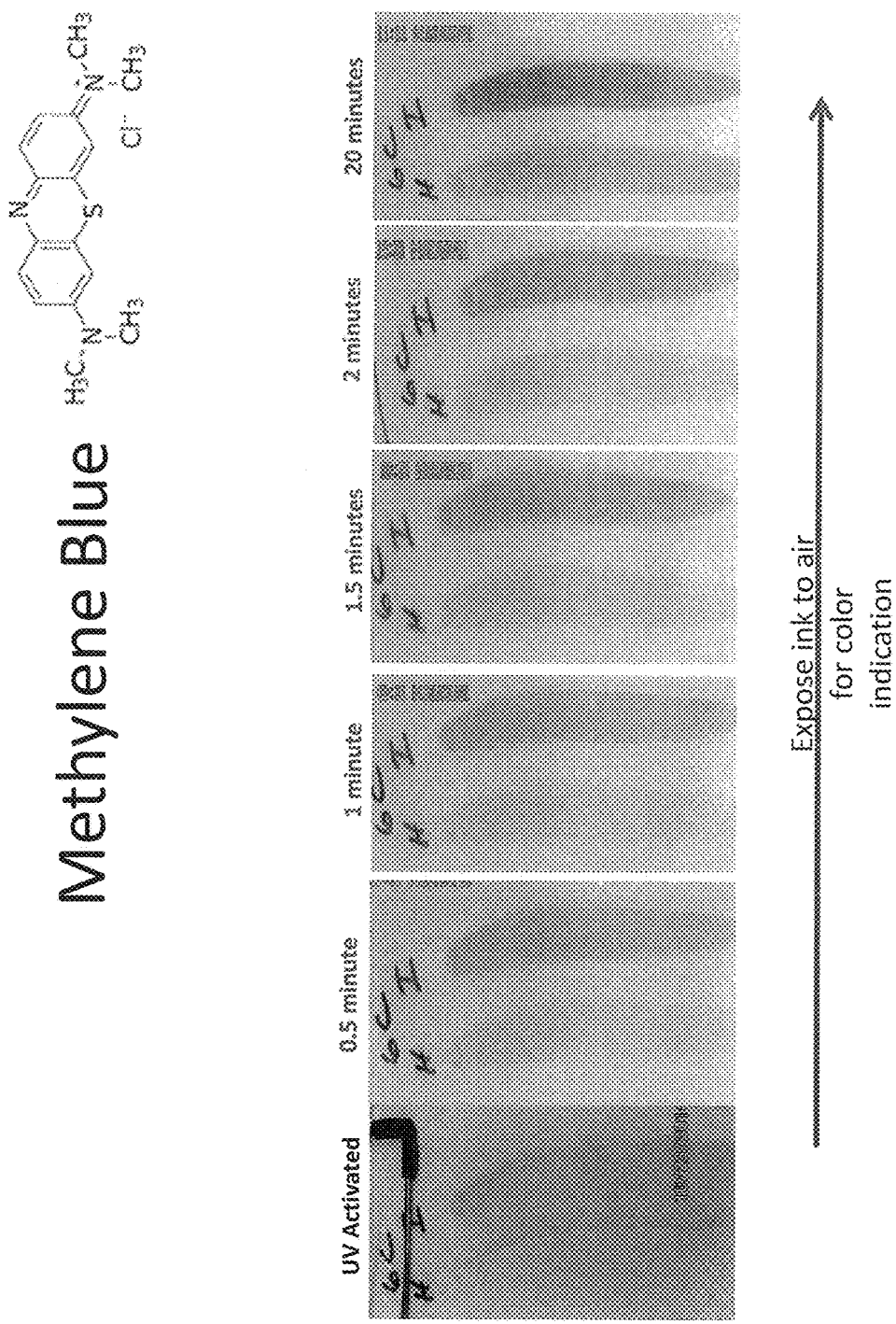
Figure 9: Air exposure of UV activated Ink 6C with MB and H/I modifications.

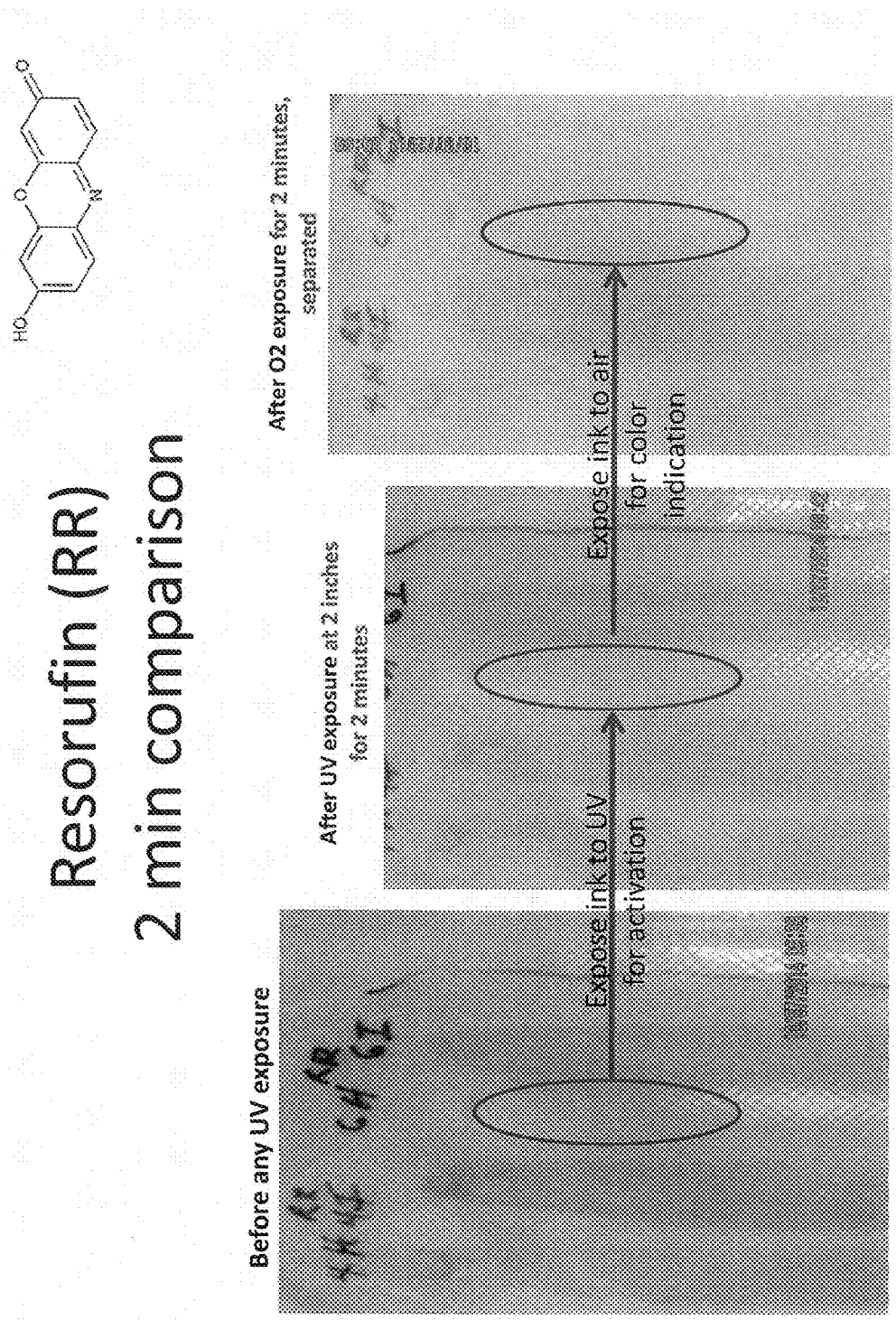
Figure 10: UV activation and air exposure (after 2 mins) of Ink 4 with RR and H/I modifications.

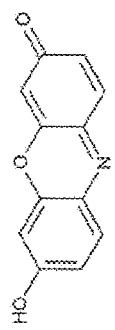
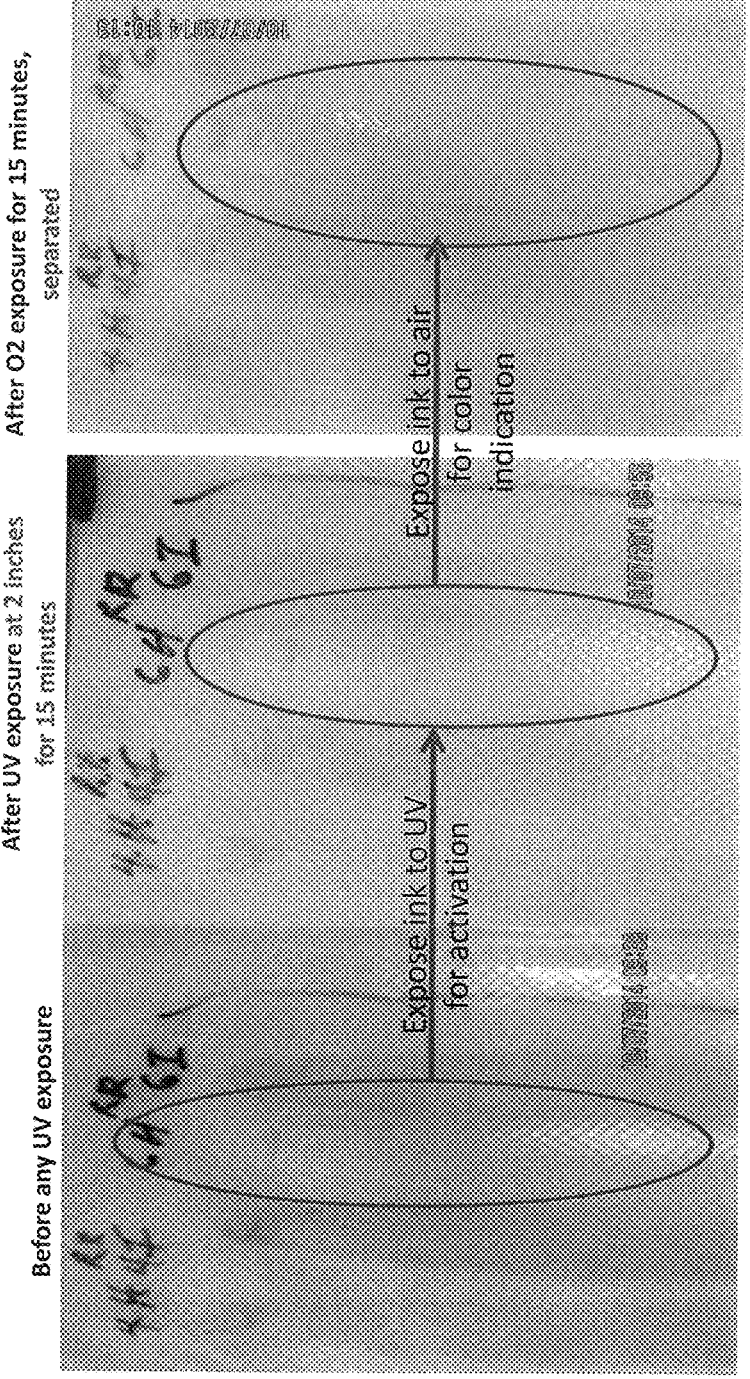
Figure 11: UV activation and air exposure (after 15 mins) of Ink 4 with RR and H/I modifications.

ABCDEFGHIJKLMN
OPQRSTUVWXYZÀÅ
ÉÏÖØÜabcdefghij
klmnopqrstuvwx
yzàåéïöøüÆ1234
567890($¢£€.,!?)

DAMAGE INDICATING PACKAGING

CROSS-REFERENCE TO RELATED APPLICATIONS

This application is a continuation-in-part of U.S. patent application Ser. No. 14/272,156 filed May 7, 2014, which claims priority from U.S. Provisional Patent Application Ser. No. 61/820,315 filed May 7, 2013 and U.S. Provisional Patent Application Ser. No. 61/971,187 filed Mar. 27, 2014. This application also claims the benefit of U.S. Provisional Patent Application Ser. No. 62/078,819 filed Nov. 12, 2014. All of these applications are incorporated herein by reference.

FIELD OF THE INVENTION

The present invention relates to damage indicating packaging for condoms and other articles such as food products and pharmaceuticals.

BACKGROUND INFORMATION

Conventional condom packaging provides an expiration date, but no obvious evidence of tampering. Air bubbles have been used in condom packaging as an indication of whether the packaging has been compromised. However, a need exists for an easy and reliable indication that condom packages have been compromised. In addition, a need exists for other types of damage indicating packaging for food products, pharmaceuticals and the like.

SUMMARY OF THE INVENTION

An embodiment of the invention provides a damage indicating material such as a reactive or responsive species in a formulation that can be incorporated into a variety of substrates. The damage indicating material may change color when exposed to oxygen, excessive heat and/or excessive pressure. The damage indicating material may include an anti-counterfeiting taggant material. One method of incorporating the reactive/responsive material can involve printing a damage indicating ink or coating on a substrate. One embodiment of the invention involves printing a reactive/responsive ink formulation on plastic films used for vacuum packaging. In one package style of this embodiment, the printed vacuum packaging is used as a vacuum sealed overwrap around an already-packaged product. Exemplary products include packaged condoms, food and pharmaceuticals.

An aspect of the present invention is to provide a damage indicating package comprising an inner wrapper layer defining an interior volume structured and arranged to receive a product, an outer layer at least partially covering the inner wrapper layer, and a damage indicating material between the inner wrapper layer and the outer wrapper layer.

Another aspect of the present invention is to provide a damage indicating packaging material comprising a film layer structured and arranged for wrapping around a product, and a damage indicating material applied to the film layer.

A further aspect of the present invention is to provide a packaged product comprising an inner wrapper layer defining an interior volume containing the product, an outer layer at least partially covering the inner wrapper layer, and a damage indicating material between the inner wrapper layer and the outer wrapper layer.

Another aspect of the present invention is to provide a method of making a damage indicating product package comprising applying a damage indicating material to a layer of material that is structured and arranged to receive a product therein.

A further aspect of the present invention is to provide a method of providing an indication that a product package has been damaged comprising wrapping the product with at least one layer having a damage indicating material applied thereto.

These and other aspects of the present invention will be more apparent from the following description.

BRIEF DESCRIPTION OF THE DRAWINGS

FIGS. 8-11 illustrate results from the examples below.

FIGS. 12 and 13 illustrate damage indicating ink printing styles in accordance with embodiments of the invention.

DETAILED DESCRIPTION

Figure 1:
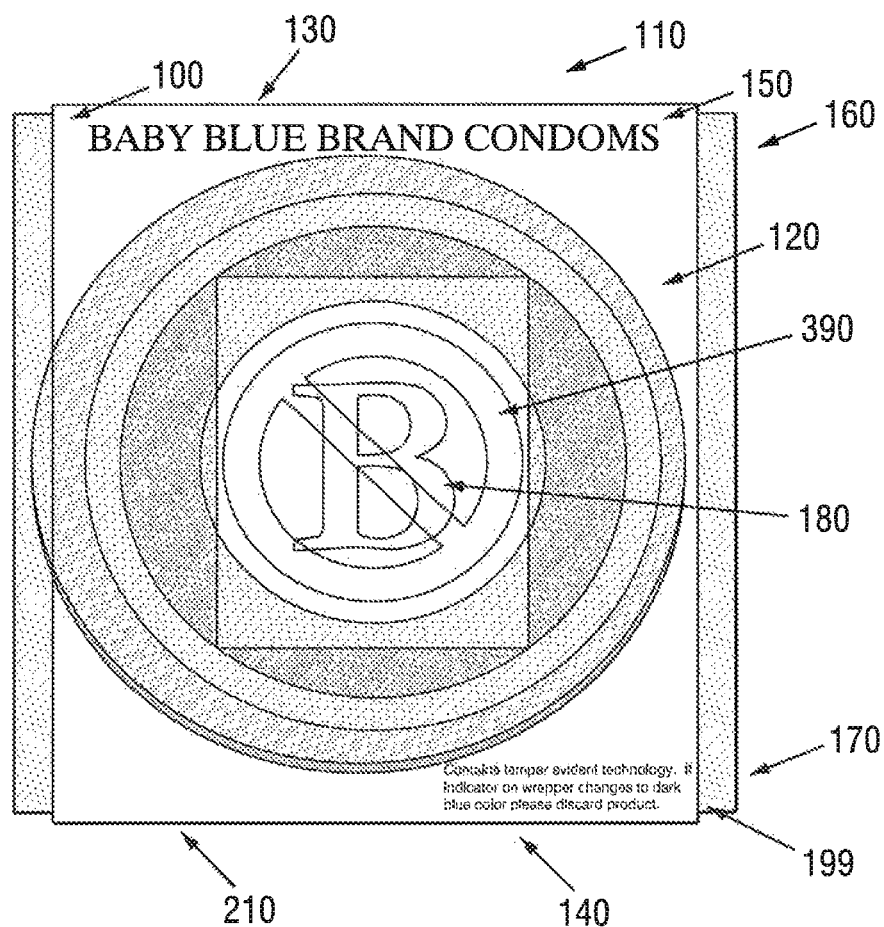
FIG. 1 is a partially schematic front view of a sealed condom package with a substantially transparent company logo and universally recognized symbol in accordance with an embodiment of the invention.

The following is a detailed description of exemplary embodiments to illustrate the principles of the invention. The embodiments are provided to illustrate aspects of the invention, but the invention is not limited to any embodiment. The scope of the invention encompasses numerous alternatives, modifications and equivalents. Numerous specific details are set forth in the following description in order to provide a thorough understanding of the invention. However, the invention may be practiced according to the claims without some or all of these specific details. For the purpose of clarity, technical material that is known in the technical fields related to the invention has not been described in detail so that the invention is not unnecessarily obscured.

An embodiment of the present invention provides active and intelligent product packaging including information printed thereon that allows anyone seeing it to know that the packaging has been compromised and to discard the product if damaged. A damage indicating material may be utilized that causes the packaging to change color when exposed to oxygen, extreme heat and/or excessive pressure such as compression or tension. The damage-indicating packaging gives the user clear indication that the product contained therein has been compromised and can be immediately discarded.

Although packaging for condoms is primarily described herein, the present invention may be used with other products to be packaged, and for other applications. Non-limiting examples include foods and beverages, pharmaceutical products and packaging (packaging, including modified atmosphere packaging, additives, coatings), life sciences (lab supplies, including bioreactors and cell cultivating flasks, medical devices, diagnostics and equipment, surgical supplies and equipment, fertility supplies and equipment, imaging oxygen distributions in biomedicine, microbiology, and imaging intra and extra-cellular oxygen distribution in biological systems), military and defense supplies and equipment, weapons, security and authentication (steganography, anti-counterfeiting, anti-piracy, microprinting, document stamps or seals, currency, stamps, security tags and seals), documents, evidence, commercial products (electronic devices such as cell phones, tablets and computers, utensils, tattoo supplies and shipping containers), high end (luxury goods, artwork, archival protection), detectors/sensors (variable oxygen content detectors, enzymatic sensors, oxygen distribution sensors), advanced packaging (biodegradable packaging, Braille-based packaging) and other advance materials (reactive and responsive materials).

In certain embodiments, the damage indicating packaging may be provided as an overwrap for a previously packaged product, such as an overwrap for pre-packaged food or pharmaceutical products. For example, pharmaceutical pills, tablets, capsules, liquids, etc. that are packaged in bottles, blister wraps and the like may be overwrapped with the damage indicating packaging. In other embodiments, the food, pharmaceutical or other product may be directly wrapped with the damage indicating packaging.

Further features of the invention provide for the information to be printed on a front and/or back layer of the packaging. The information may include any one or more of manufacturing information, artwork, text, logos, slogans, insignia, instructions or the like.

An embodiment of the invention also provides a process for manufacturing damage-indicating packaging with a film layer of plastic, foil, paper or the like having a damage indicating material applied thereto. The packaging film layer and damage indicating material may be exposed to electromagnetic radiation, which renders the damage indicating material substantially colorless. In certain embodiments, the damage indicating material may be added to a layer of the packaging prior to the product being inserted and the packaging being sealed. A sealing unit may seal the package layers together around each product and dispense the packaged products either individually or in strips. The sealing unit may also print manufacturing information on the sealed packages.

Figure 2:
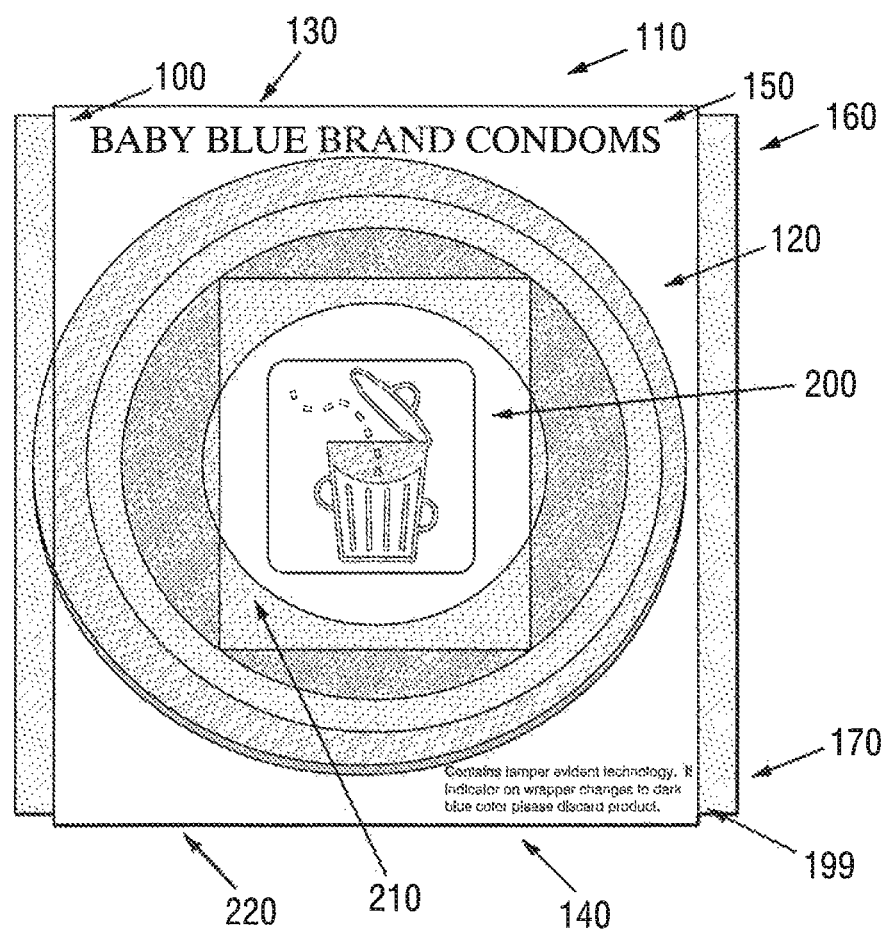
FIG. 2 is a partially schematic back view of the sealed condom package of FIG. 1 showing a substantially transparent universal throwaway symbol in accordance with an embodiment of the invention.

Referring now to an embodiment of the invention in more detail, in FIGS. 1 and 2, the combination of a condom and a package therefor is schematically shown at 100. The combination comprises a package shown generally at 110, and a rolled condom shown generally at 120. The package comprises a front wrapper panel or layer 130 and a back wrapper panel or layer 140. The front 130 and back 140 wrapper layers are sealed to one another around their respective edges. Labeling is shown generally at 150. Package instructions are shown generally at 199. In the embodiment shown, the instructions 199 state "Contains tamper evident technology. If indicator on wrapper changes to dark blue color please discard product". As shown in FIG. 1, a front outer layer 210 covers the front wrapper layer 130. A damage indicating material is applied on the front outer layer 210. As shown in FIG. 2, a back outer layer 220 covers the back wrapper layer 140, and a damage indicating material is applied on the back outer layer 220.

Still referring to FIGS. 1 and 2, universal symbols 190, 200 and a company logo 180 are printed on the package with a damage indicating material that includes a reactive dye such as methylene blue, alternative oxygen sensitive reactive dye, or alternative damage indicating material on package interiors, and processed to convert them to a colorless or different colored form. When the reactive damage indicating material is subsequently activated by exposure to oxygen, extreme heat, or excessive pressure, such as compression or tension, it changes in appearance. For example, the reactive damage indicating material changes color when exposed to oxygen. The color change should be sufficiently stable such that the color is visible for a sufficiently long time period. In certain embodiments, the long-term stability may be for periods of days, weeks, months or years.

Figure 3:
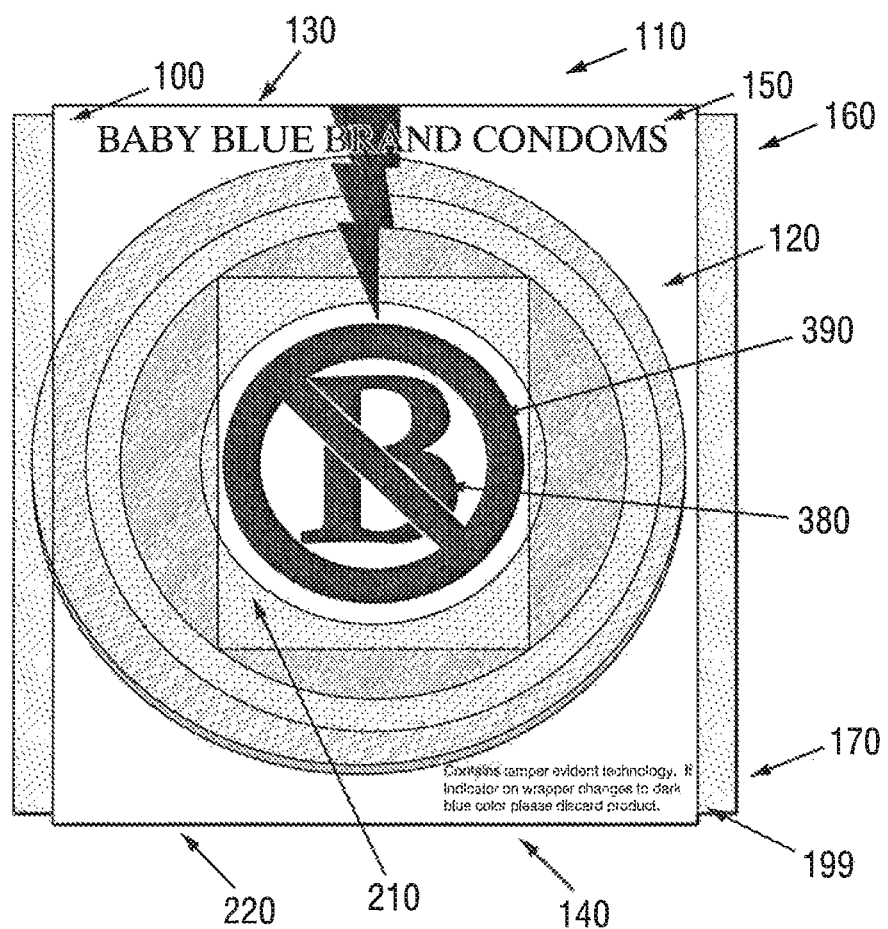
FIG. 3 is a partially schematic front view of a condom package once exposed to oxygen with tamper evident coloring displaying a universally recognized symbol as a result of color bloom of a damage indicating material in accordance with an embodiment of the present invention.
Figure 4:
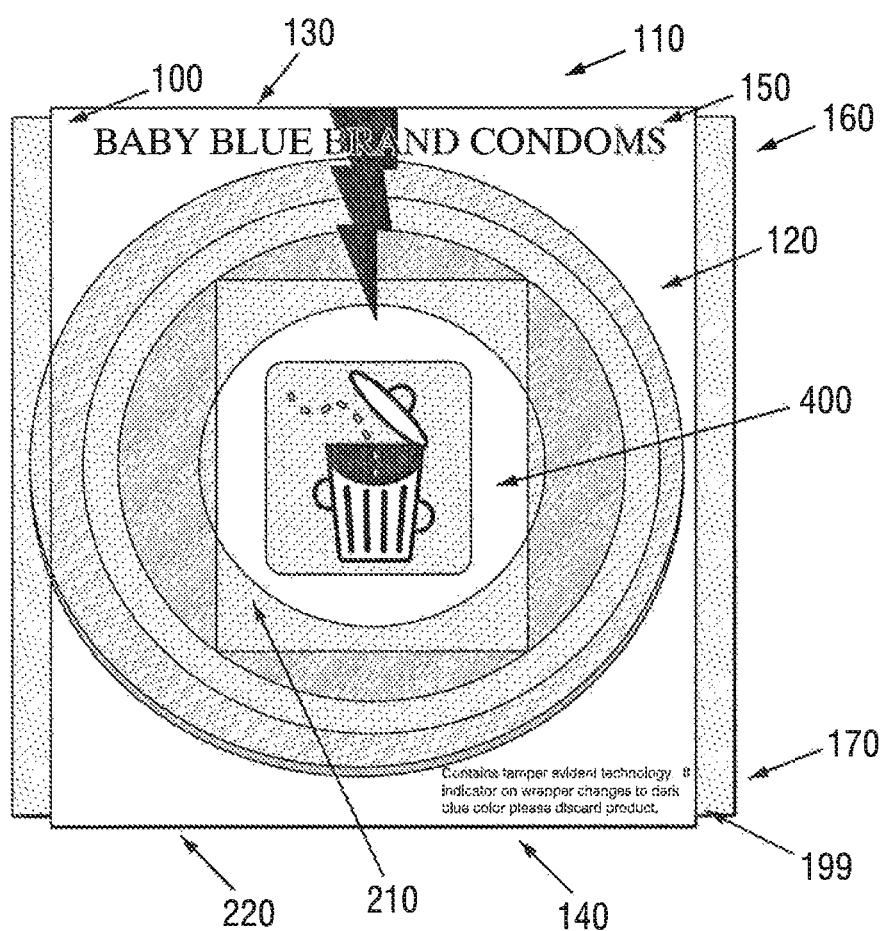
FIG. 4 is a partially schematic back view of the condom package of FIG. 3 once exposed to oxygen with tamper evident coloring displaying a universally recognized symbol or customized symbol as a result of the color bloom of the damage indicating material in accordance with an embodiment of the present invention.

FIGS. 3 and 4 schematically illustrate the condom package 100 in a damage-indicating state in which the condom wrapper has been torn. The universal symbols 390, 400 and company logo 380 are re-oxidized and change color (in the case of methylene blue) due to exposure to oxygen, or bloom with color due to extreme heat, excessive pressure, compression or tension. Re-oxidation is indicated with a color bloom of the universal symbols 390, 400 and company logo 380.

It will be understood that the rolled condom 120 as shown in FIGS. 1-4 has an open end 160 and a closed end 170. However, the precise details of the condom 120 are not relevant to the present invention, e.g., the condom may be pre-lubricated or not, may have a tip for collection of ejaculate, etc.

Figure 5:
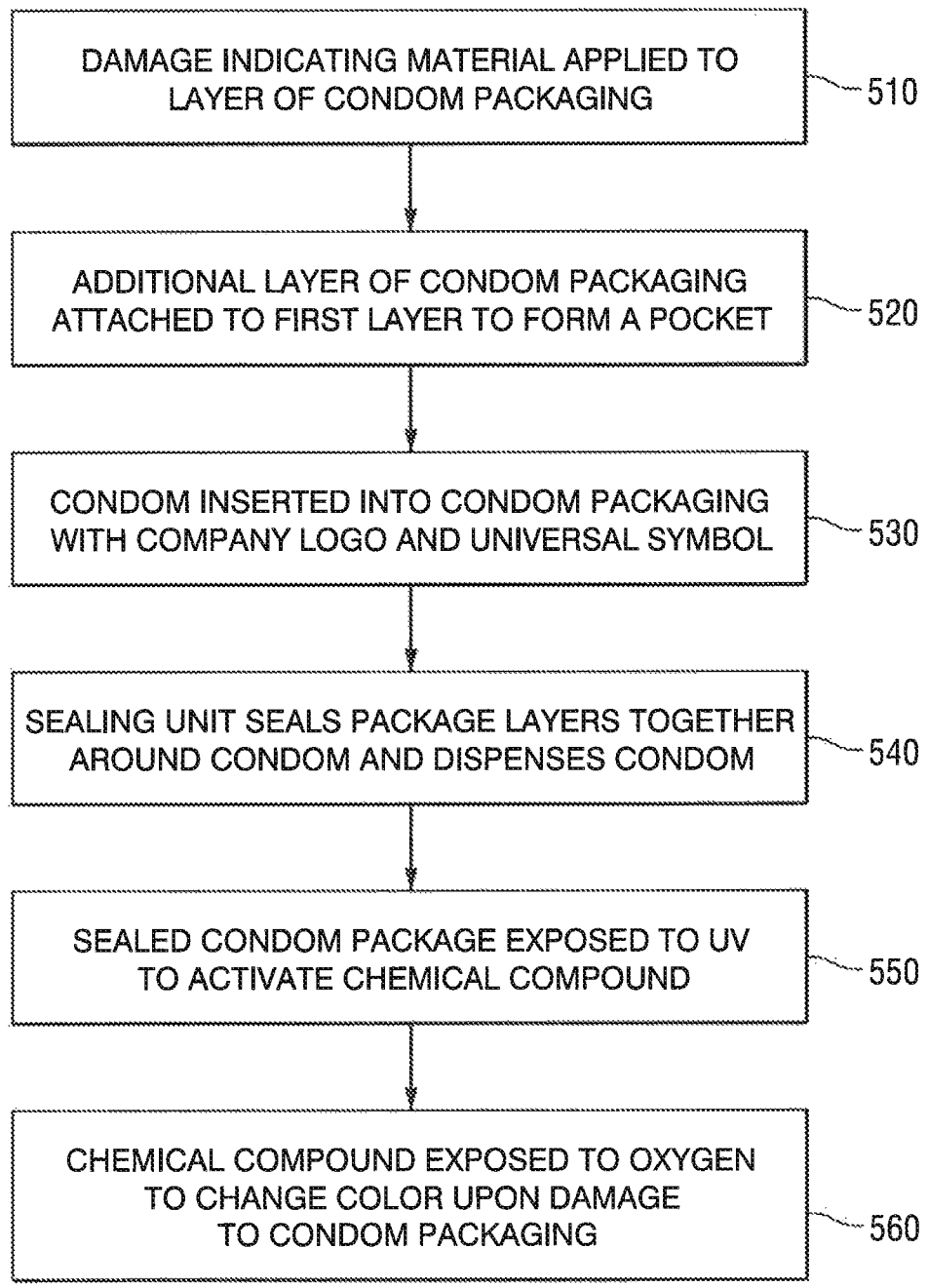
FIG. 5 is the flow diagram illustrating a method of making a damage indicating condom package in accordance with an embodiment of the invention.

FIG. 5 is a flow diagram illustrating a method of making a damage evident condom package in accordance with an embodiment of the present invention. In step 510, the interior wall of a condom packaging layer is coated with a damage indicating material such as methylene blue, any suitable alternative oxygen-sensitive reactive dyes, or responsive, color-changing material combination. The material may be applied by any suitable means such as spraying, brushing, screen printing, ink jet printing or the like. Methylene blue dye may be used in the printing process. Other responsive materials may be thiazines, thionines, oxazines, azines, triphenylmethane, indophenol, indigo, thioindigo, pyridinium viologens, and quinone-based species. Additional responsive materials may be non-toxic phosphorous pigmentation, or any alternative oxygen sensitive reactive dyes or any dyes that change color when exposed to oxygen, extreme heat, or excessive pressure, compression or tension. The responsive, damage indicating material may comprise more than one type of reactive dye. There will be associative processes to prepare the oxygen sensitive reactive dyes to reduce it to a colorless form. The printer may be of conventional construction and operation and sprays dye onto the packaging. The manufacturing information is provided by a processor (not shown), the operation of which is not germane to this invention, and which also controls printing by the sealing unit.

In step 520, another layer, which may also have damage indicating material applied thereto, is sealed or otherwise attached to the layer formed in step 510, e.g., to thereby form a pocket.

In step 530, a condom is inserted into the condom package or pocket. The condom may optionally be pre-wrapped in any suitable type of wrapper prior to insertion into the pocket. A company logo and/or universal symbols may be printed on one or more of the layers of packaging.

In step 540, a sealing unit seals the package layers together around each condom 120 and dispenses the condoms either individually or in strips.

In step 550, the sealed condom package is exposed to electromagnetic radiation, such as ultraviolet radiation or any other radiation of suitable wavelength, e.g., to render the damage indicating material substantially colorless.

In step 560, the chemical compound is exposed to oxygen to change the color of the damage indicating material by oxidation or another type of chemical reaction that changes the reactive dye from colorless to colored or from one color to another upon tampering, extreme heat, excessive pressure, compression, tension or any other breach of the condom wrapper such as a tear, pin-prick, or intentionally opening condom packaging. Printing between the layers of packaging prevents the dye from coming into contact with the condom. Is thus not possible for a user to experience any reaction due to contact with the dye.

Figure 6:
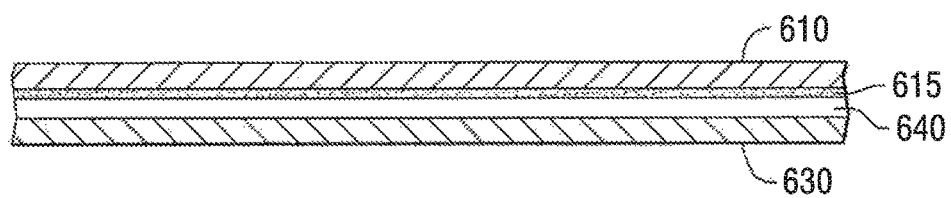
FIG. 6 is a partially schematic side sectional view showing a portion of a condom packaging material in accordance with an embodiment of the present invention.
Figure 7:
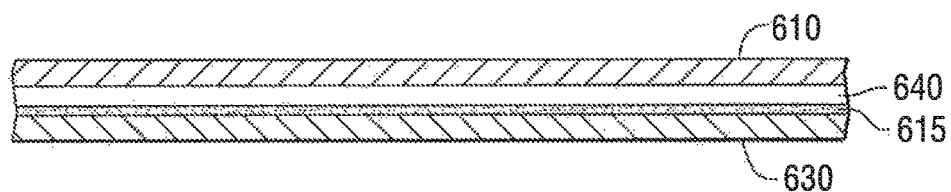
FIG. 7 is a partially schematic side sectional view showing a portion of a condom packaging material in accordance with another embodiment of the present invention.

FIGS. 6 and 7 are partially schematic side sectional views illustrating various condom packaging layers in accordance with embodiments of the present invention. In FIG. 6, an outer layer 610 is provided with a layer of damage indicating material 615 applied thereto. An inner condom wrapper layer 630 is located adjacent to the outer layer 610 and damage indicating material 615. In certain embodiments, the inner wrapper layer 630 may not be adhered to the layer of damage indicating material 615, as shown by the gap 640 in FIG. 6. Although the gap 640 is shown as a physical spacing between the layers 630 and 615 in FIG. 6, it should be recognized that the gap may be closed such that the layers 630 and 615 contact each other. For example, when the space between the outer layer 610 and inner wrapper layer 630 is evacuated, the layer of damage indicating material 615 would typically contact the underlying inner wrapper layer 630. Alternatively, when the space between the outer layer 610 and inner wrapper layer 630 is filled with an inert or non-reactive gas, the pressure of the gas may result in the formation of a physical gap 640, as shown in FIG. 6.

The embodiment shown in FIG. 7 is similar to the embodiment of FIG. 6, except the layer of damage indicating material 615 is applied to the outer surface of the inner wrapper layer 630 rather than the inner surface of the outer layer 610.

In accordance with embodiments of the present invention, the various inner condom wrapper layers and outer layers may be made of any suitable materials such as polymeric films, foils, paper and the like. Some examples of polymeric layers include cellulosic materials, vinyl polymers such as polyvinyl alcohol and polyacrylates, polyolefins such as polyethylene, polyethylene terephthalate (PET), ethylene vinyl acetate copolymers, polyethylene, nylon (polyamide) and the like. The inner wrapper layers and outer layers may be made of the same or different materials. In certain embodiments, the inner wrapper layers may comprise foil coated with any of the aforementioned polymers, or such polymers alone. In certain embodiments, the outer layers may comprise polyethylene or the like, which may optionally be coextruded with nylon or the like.

In an embodiment of the invention, a condom or other product is disposed in an inner wrapper, an outer wrapper surrounds the inner wrapper, and a layer of damage indicating material is applied to the inner surface of the outer wrapper. Alternatively, as described above, the outer surface of the inner wrapper may have the damage indicating material applied thereto. In both of these embodiments, the space between the inner and outer wrappers may be evacuated by any suitable type of vacuum source in order to remove gasses including oxygen from the space between the wrappers. In this embodiment, when the outer wrapper is punctured, torn or otherwise breached, air will fill the previously evacuated space between the inner and outer wrappers, thereby coming into contact with the relatively large surface areas of the wrappers, i.e., the outer surface of the inner wrapper will be exposed to air and the inner surface of the outer wrapper will be exposed to air. The presence of the damage indicating material on the inner surface of the outer wrapper and/or on the outer surface of the inner wrapper will thereby provide an indication that the outer wrapper has been punctured, torn or otherwise breached and that air has entered the space between the wrappers. As an alternative to evacuating the space between the inner and outer wrappers, the inner space may be at least partially filled with an inert or non-reactive gas such as nitrogen or the like that does not cause the damage indicating material to react and change colors.

In accordance with an embodiment of the present invention, dual-wrapper arrangements as described above may be made by providing a pre-packaged condom or other product in the inner wrapper, followed by applying the outer wrapper around the inner wrapper. For example, the outer wrapper may be provided as a pre-formed pocket in which the inner wrapper containing the product is inserted, followed by sealing of the open end of the outer wrapper. As discussed above, before, during or after the sealing operation, the space between the inner and outer wrappers may be evacuated and/or filled with a non-reactive gas. As another example, separate sheets of outer wrapper material may be placed on opposite sides of the inner wrapper containing the product, following by sealing of the peripheral edges of the outer wrapper layers together to thereby seal the inner wrapper and product within the outer wrapper. Again, the space between the inner and outer wrappers may be evacuated and/or filled with a non-reactive gas during the sealing operation. Such operations, in which the product is first sealed in the inner wrapper followed by sealing an outer wrapper around the inner wrapper, may be conducted contemporaneously with each other, e.g., the inner and outer wrappers may be applied in the same manufacturing operation. Alternatively, pre-packaged products may be modified by applying the outer wrapper at a different time or location, e.g., at a different facility from the original product manufacturing location.

In accordance with another embodiment of the present invention, a single product wrapper is provided with multiple laminated layers in which at least one of the layers contains the damage indicating material. For example, a layer of damage indicating material may be sandwiched between inner and outer polymeric layers to provide a composite wrapper structure with damage indicating capabilities. As another example, a layer of damage indicating material may be applied on the inner surface of the single product wrapper. In this embodiment, the damage indicating material layer would be exposed to the product, and the damage indicating material must be non-reactive with the material of the product or any other liquids or gasses contained within the wrapper, and the damage indicating layer must not damage the product or vice versa.

The damage indicating material may comprise an absorption-based species that produces a visible color change caused by chromogenic chemistry that involves oxidation by molecular oxygen. Examples include methylene blue, resorufin, resazurin, thiazine, thionines, oxazine, azine, triphenylmethane, indophenol, indigo, thioindigo, pyridinium viologen, and quinone-based species. The damage indicating material may also comprise luminescence-based species such as polycyclic aromatic hydrocarbons, polypyridyl complexes, metalloporphyrins, including platinum and palladium complexes, cyclometallated complexes, and other luminescent metal complexes such as lead, aluminum, copper, gold, europium, terbium, molybdenum, and the like. Other damage indicating material species include fullerenes, fluorescent polymers, and modified polymeric materials containing absorption-based or luminescence-based species described above. Additional responsive materials may be non-toxic phosphorous pigmentation, or any alternative oxygen sensitive reactive dyes or any dyes that change color when exposed to oxygen, extreme heat, or excessive pressure, compression or tension.

The reactive/responsive species can be incorporated into a variety of formulations including inks, gels, plastics, composites and the like Ink formulations include resin/binder variations such as gelatin, cellulosics such as hydroxyethylcellulose (HEC), ethyl cellulose, cellulose acetate, polyvinylalcohol (PVA), polyvinylpyrolidone (PVP), polyamides, polyurethanes, polyethylene oxide (PEO), poly acrylates such as polymethyl methacrylate (PMMA), polymethacrylate, and polystyrene or modified polystyrenes. The ink formulations may include inks typically used on plastic films and vacuum packaging films, or for pad printing, flexo printing, gravure printing, dot matrix style printing, steganography printing, and the like. Semiconductor variations include oxides of titanium, tin, tungsten, zinc and/or mixtures thereof. Semiconductor size variations include submicron diameter, sub 50 nm diameter, and sub 10 nm diameter. Sacrificial electron donor variations may be a mild reducing agent, amine such as sodium salt of ethylenediaminetetraacetic acid (NaEDTA) or triethanolamine (TEOA), saccharide such as glucose or fructose, antioxidant such as ascorbic acid or citric acid, or other easily oxidizable species such as glycerin or oxidizable polymer such as polyvinylalcohol (PVA). Additive variations include solubility modifiers such as surfactants, permeability modifiers such as silicones, and modifiers for oxygen transmissibility rate (OTR) or water vapor transmissibility rate (WVTR). Examples of additives include moisture absorbers, oxygen scavengers, microwave susceptors and antimicrobials.

In certain embodiments, anti-counterfeiting taggant materials may be added to the formulations in order to authenticate the product in order to protect against counterfeiting. Known types of taggants may be added to the damage indicating material. For example, taggant particles or compositions may be added to coatings, inks and adhesives, or embedded in packaging layers and/or labels. Types of anti-counterfeiting taggant materials include infrared (IR) responsive particles and inks, ultraviolet (UV) responsive particles and inks, secure pigments, metachromic materials, color-shift materials, thermochromic materials, and the like. A non-limiting example of commercially available taggants that may be added to, or used in association with, the damage indicating materials of the present invention is a particulate taggant material sold under the designation Microtaggant by Microtrace, LLC. Other types of commercially available taggant materials include SunGuard inks sold by Sun Chemical Corporation. When taggant particles or compositions are added to the present damage indicating coatings, they may typically be present in amounts ranging from a minimal detectable trace amount up to 5 or 10 weight percent of the coating, or more. For example, taggants may comprise from 0.001 to 5 weight percent, or from 0.01 to 2 weight percent, or from 0.1 to 1 weight percent of the material.

Other embodiments of substrate types include glass, plastic, organic composites (binder such as cellulose, polymers, etc.), inorganic composites (binder such a zeolite, silica gel, etc.), and nanocomposites. Other embodiments of formulations include multi-layer plastic films, filled reinforced plastic composites, and filled non-reinforcing plastic composites.

The damage indicating material may be printed or applied to a packaging substrate by any suitable means such as spraying, screen printing, brushing, immersion, ink jet printing, or the like. Various printing variations may be used for the damage indicating inks, such as variable coating thicknesses, and variable coating line widths. A micro dot or dot matrix style to increase surface area of ink within overall mark is illustrated in FIG. 12. A cross hatch style to increase surface area of ink within overall mark is illustrated in FIG. 13.

The packaging in its completed form may have a company logo displayed clear on one side and a clear icon of a trashcan on the reverse side. If opened for intended use or accidentally or intentionally pricked exposing the product inside, exposed to extreme heat, or excessive compression or tension, the coloring of the packaging will change, highlighting the company logo with universal "NO" symbols emblazoned over it, including, but not limited to the symbols for "Do not Enter", "Prohibited", an "X", a circle, square, triangle with a backslash or line going through it, horizontally, vertically, or diagonally, a stop sign, a hand, trash can or customized symbol. On the reverse side a trash can icon or alternative customized symbol(s) will also color change indicating that the packaging and the product contained within should be thrown away. In certain embodiments, anti-counterfeiting indicia may be printed or otherwise applied to the packaging and/or labels applied to the packaging.

The disclosed embodiments are illustrative, not restrictive. While specific configurations including a packaged condom have been described, it is understood that the present invention can be applied to a wide variety of other packaging for other types of products including paper, foils, or plastics, as well as any combination thereof, such as foil-lined paper, plastic-lined paper or a wax-lined paper. The package may take a variety of forms such as rectangular, oval, etc., or can be male or female condom packaging, or packaging for other types of products. The package may be provided with a separation structure, such as an edge tear area, a zipper-locked edge area, or an openable, adhesively sealed edge area. There are many alternative ways of implementing the invention. Alternative embodiments include transparent or translucent plastic lids, transparent or translucent plastic containers. Plastics can be LDPE, HDPE, PP, or a combination of plastics including, but not limited to polycarbonates, or acrylics.

Package style embodiments include vacuum-sealed overwrap, vacuum-sealed overwrap with interior printed surface, vacuum-sealed overwrap with printed coupon between item and interior overwrap surface, vacuum-sealed overwrap containing multi-layer plastic with oxygen-indicating ink added as an internal layer, and vacuum-sealed overwrap containing multi-layer plastic with oxygen-indicating ink compounded into plastic material comprising at least one layer of the multi-layer film.

The following examples are intended to illustrate various aspects of the present invention, and are not intended to limit the scope of the invention.

EXAMPLE 1

A damage indicating material was made as follows. Ten grams of 5% aqueous solution of hydroxyethylcellulose (HEC) and 2.5 grams of 5% aqueous dispersion of titanium dioxide ($TiO_2$) were added to a 20 mL amber glass scintillation vial. The mixture was sonicated for approximately 30 minutes in a warm ultrasonic bath. After dispersing the $TiO_2$, 0.5 grams of 5% aqueous solution of methylene blue (MB) was added to the mixture. The mixture was sonicated or magnetically stirred for 10-15 minutes to disperse the MB in the aqueous mixture. After dispersing the MB into the mixture, 0.15 g of triethanolamine (TEOA) were added using a plastic or glass pipet. The final formulation was sonicated for approximately 30 minutes in a warm ultrasonic bath prior to substrate application.

The formulation was applied as a thin layer of glass or plastic film substrate and was allowed to dry. Standard laboratory glass microscope slides and 3 mil thick co-extruded polyethylene-nylon vacuum packaging film were used as substrates for coating. The plastic film was also used as an overwrap to seal the coated glass slides or plastic film prior to activation and deactivation. The formulation was typically applied by painting a thin film on the substrate with a paint brush. Uniform film casting can also be accomplished using a spin coater or K bar techniques. The coated substrates were allowed to dry within a dark oven set at 50° C. for 16 hours. The resultant blue layer had a dry-film thickness of approximately 2 mils or less with variations in thickness dependent on the exact formulation. The dried, blue films of damage indicating material were vacuum sealed within a plastic film overwrap. Following evacuation and thermal sealing, the material was "activated" under a UV lamp to convert the blue MB form to a white leuco MB form. Upon such UV exposure, the layer changed from substantially blue to off-white or light gray. After activation, the layer was exposed to air by puncturing or cutting open the vacuum overwrap, resulting in a change back to the blue color. After the color transformation, the layer retained a significant degree of its blue color for over several weeks.

The formulations in Examples 2 through 8 used commercial ink formulations for flexo and gravure printing by Siegwerks (Ink 4 and Ink 6) Ink 6 was also modified for this work to give Ink 6A with no water, ink 6B with no water or titanium dioxide, ink 6C with no water and nano titanium oxide and ink 6D with no water and additives to increase oxygen permeability. Thus, the six different starting ink formulations are Ink 4, 6, 6A, 6B, 6C and 6D. Modifications to the starting ink formulations yield reactive/responsive, damage indicating materials. The Reactive/responsive, damage indicating materials are labeled as Ink X-Y where X=4, 6A, 6B, 6C, 6D and Y=A through J.

A reactive/responsive ink formulation was made as follows. Two grams of well mixed ink formulation (Ink 4, 6A, 6B, 6C or 6D) were added to a 20 mL amber glass scintillation vial. Then 0.01-0.02 grams of the reactive/responsive species (methylene blue=MB) was weighed into the vial. Finally 0.10-0.80 grams of a sacrificial electron donor (TEOA) was weighed into the vial. A magnetic stir bar was added to the vial and the mixture was stirred and/or ultrasonicated until the dye was well dissolved or dispersed (half hour to 24 hours).

Prior to printing, the substrate was dried to remove any residual moisture. The substrate was a 75 micron thick, 2 layer co-extruded film composed of nylon and polyethylene. A small amount of the reactive/responsive ink formulation was applied to the dried substrate. A K-Bar (#0, #2 or #6) was used to achieve a uniform film thickness. The ink was drawn down with the K-Bar using steady, constant pressure and speed. The printed substrate was dried in a 50 degree Celsius oven until the ink set (1 hour to 24 hours). The dried printed substrate was evacuated and heat sealed using a commercial vacuum sealer. In one package style of this embodiment, the dried printed substrate is used as a vacuum sealed overwrap around an already-packaged product such as a packaged condom.

The reactive/responsive ink formulation on the dried, printed and vacuum-sealed substrate was activated with UV light. The UV lamp was allowed to warm up for at least 1 hour so that the UV intensity was stable and consistent. The ink was UV activated by exposing the printed and sealed substrate at a set distance (3 inches) and intensity (~10 mW/cm2 with 1 hour warm up) to achieve a stable color change. The MB changes from blue to the colorless leuco form. After activation, the layer was exposed to air by puncturing or cutting open the vacuum-sealed overwrap. Color change was monitored over the course of approximately 20 minutes. The color started to change with the first minute after exposure.

EXAMPLE 2

Reactive/responsive, damage indicating materials were made using Ink 6 with methylene blue (MB) as the reactive/responsive species and triethanolamine (TEOA) as the sacrificial electron donor as set forth in Table 1. Quantities are in grams. The damage indicating material was made as follows. Two grams of well mixed Ink 6 were added to a 20 mL amber glass scintillation vial. Then 0.01-0.02 grams of the reactive/responsive species (methylene blue=MB) was weighed into the vial. Finally 0.10-0.80 grams of a sacrificial electron donor (TEOA) was weighed into the vial. A magnetic stir bar was added to the vial and the mixture was stirred and/or ultrasonicated until the dye was well dissolved or dispersed (half hour to 24 hours).

Prior to printing, the substrate was dried to remove any residual moisture. The substrate was a 75 micron thick, 2 layer co-extruded film composed of nylon and polyethylene. A small amount of the reactive/responsive ink formulation was applied to the dried substrate. A K-Bar (#0, #2 or #6) was used to achieve a uniform film thickness. The ink was drawn down with the K-Bar using steady, constant pressure and speed. The printed substrate was dried in a 50 degree Celsius oven until the ink set (1 hour to 24 hours). The dried printed substrate was evacuated and heat sealed using a commercial vacuum sealer. In one package style of this embodiment, the dried printed substrate is used as a vacuum sealed overwrap around an already-packaged product such as a packaged condom.

The damage indicating material was activated on the dried, printed and vacuum-sealed substrate with UV light. The UV lamp was allowed to warm up for at least 1 hour so that the UV intensity was stable and consistent. The ink was UV activated by exposing the printed and sealed substrate at a set distance (3 inches) and intensity (~10 mW/cm2 with 1 hour warm up) to achieve a stable color change. The MB changes from blue to the colorless leuco form. After activation, the layer was exposed to air by puncturing or cutting open the vacuum-sealed overwrap. Color change was monitored over the course of approximately 20 minutes. The color started to change with the first minute after exposure.

TABLE 1

| Formulation | Ink 6 | MB | moles MB | TEOA | moles TEOA | moles SED/ moles MB | moles SED/ moles MB per g ink |
|---|---|---|---|---|---|---|---|
| A | 2 | 0.1 | 0.0002675 | 0 | 0 | 0 | 0 |
| B | 2 | 0.1 | 0.0002675 | 0.1 | 0.00067 | 2.5 | 1.3 |
| C | 2 | 0.02 | 0.0000535 | 0.2 | 0.001341 | 25.1 | 12.5 |
| D | 2 | 0.02 | 0.0000535 | 0.4 | 0.002681 | 50.1 | 25.1 |
| H | 2 | 0.01 | 0.0000267 | 0.2 | 0.001341 | 50.1 | 25.1 |
| I | 2 | 0.01 | 0.0000267 | 0.4 | 0.002681 | 100.2 | 50.1 |
| J | 2 | 0.01 | 0.0000267 | 0.8 | 0.005362 | 200.5 | 100.2 |

EXAMPLE 3

Reactive/responsive, damage indicating materials were made using Ink 6 with methylene blue (MB) as the reactive/responsive species and glycerol as the sacrificial electron donor as set forth in Table 2. Quantities are in grams. The damage indicating material was made as described in Example 2.

TABLE 2

| Formulation | Ink 6 | MB | moles MB | glycerol | moles glycerol | moles SED/ moles MB | moles SED/ moles MB per g ink |
|---|---|---|---|---|---|---|---|
| E | 1 | 0.1 | 0.0002675 | 0.062 | 0.000673 | 2.5 | 2.5 |
| F | 1 | 0.01 | 0.0000267 | 0.062 | 0.000673 | 25.2 | 25.2 |
| G | 1 | 0.01 | 0.0000267 | 0.124 | 0.001347 | 50.3 | 50.3 |

EXAMPLE 4

Reactive/responsive, damage indicating materials were made using Ink 6 with resorufin (RR) as the reactive/responsive species and triethanolamine (TEOA) as the sacrificial electron donor as set forth in Table 3. Quantities are in grams. The damage indicating material was made as described in Example 2.

TABLE 3

| Formulation | Ink 4 | RR | moles RR | TEOA | moles TEOA | moles SED/ moles RR | moles SED/ moles RR per g ink |
|---|---|---|---|---|---|---|---|
| H | 2 | 0.006 | 0.0000267 | 0.2 | 0.001341 | 50.1 | 25.1 |
| H2 | 2 | 0.011 | 0.0000535 | 0.2 | 0.001341 | 25.1 | 12.5 |
| I | 2 | 0.006 | 0.0000267 | 0.4 | 0.002681 | 100.2 | 50.1 |

EXAMPLE 5

Reactive/responsive, damage indicating materials were made using Ink 4 with resorufin (RR) as the reactive/responsive species and triethanolamine (TEOA) as the sacrificial electron donor as set forth in Table 4. Quantities are in grams. The damage indicating material was made as described in Example 2.

TABLE 4

| Formulation | Ink 4 | RR | moles RR | TEOA | moles TEOA | moles SED/ moles RR | moles SED/ moles RR per g ink |
|---|---|---|---|---|---|---|---|
| H | 2 | 0.006 | 0.0000267 | 0.2 | 0.001341 | 50.1 | 25.1 |
| H2 | 2 | 0.011 | 0.0000535 | 0.2 | 0.001341 | 25.1 | 12.5 |
| I | 2 | 0.006 | 0.0000267 | 0.4 | 0.002681 | 100.2 | 50.1 |

EXAMPLE 6

Reactive/responsive, damage indicating materials were made using Ink 6A, 6C and 6D with methylene blue (MB) as the reactive/responsive species and triethanolamine (TEOA) as the sacrificial electron donor as set forth in Table 5. Quantities are in grams. The damage indicating material was made as described in Example 2.

TABLE 5

| Formulation | Ink 6A | MB | moles MB | TEOA | moles TEOA | moles SED/ moles MB | moles SED/ moles MB per g ink |
|---|---|---|---|---|---|---|---|
| H | 2 | 0.01 | 0.0000267 | 0.2 | 0.001341 | 50.1 | 25.1 |
| I | 2 | 0.01 | 0.0000267 | 0.4 | 0.002681 | 100.2 | 50.1 |

| Formulation | Ink 6C | MB | moles MB | TEOA | moles TEOA | moles SED/ moles MB | moles SED/ moles MB per g ink |
|---|---|---|---|---|---|---|---|
| H | 2 | 0.01 | 0.0000267 | 0.2 | 0.001341 | 50.1 | 25.1 |
| I | 2 | 0.01 | 0.0000267 | 0.4 | 0.002681 | 100.2 | 50.1 |

| Formulation | Ink 6D | MB | moles MB | TEOA | moles TEOA | moles SED/ moles MB | moles SED/ moles MB per g ink |
|---|---|---|---|---|---|---|---|
| H | 2 | 0.01 | 0.0000267 | 0.2 | 0.001341 | 50.1 | 25.1 |
| I | 2 | 0.01 | 0.0000267 | 0.4 | 0.002681 | 100.2 | 50.1 |

EXAMPLE 7

Reactive/responsive, damage indicating materials were made using Ink 6A and 6D with resorufin (RR) as the reactive/responsive species and triethanolamine (TEOA) as the sacrificial electron donor as set forth in Table 6. Quantities are in grams. The damage indicating material was made as described in Example 2.

TABLE 6

| Formulation | Ink 6A | RR | moles RR | TEOA | moles TEOA | moles SED/ moles RR | moles SED/ moles RR per g ink |
|---|---|---|---|---|---|---|---|
| H | 2 | 0.006 | 0.0000267 | 0.2 | 0.001341 | 50.1 | 25.1 |

| Formulation | Ink 6D | RR | moles RR | TEOA | moles TEOA | moles SED/ moles RR | moles SED/ moles RR per g ink |
|---|---|---|---|---|---|---|---|
| H | 2 | 0.006 | 0.0000267 | 0.2 | 0.001341 | 50.1 | 25.1 |

EXAMPLE 8

Reactive/responsive, damage indicating materials were made using Ink 6C with resorufin (RR) as the reactive/responsive species and triethanolamine (TEOA) as the sacrificial electron donor as set forth in Table 7. Response was modulated with dilute acetic acid and dilute ammonium hydroxide. Quantities are in grams. The damage indicating material was made as described in Example 2.

TABLE 7

| Formulation | Ink 6C | RR | moles RR | TEOA | moles TEOA | moles SED/ moles RR | moles SED/ moles RR per g ink |
|---|---|---|---|---|---|---|---|
| H | 2 | 0.006 | 0.0000267 | 0.2 | 0.001341 | 50.1 | 25.1 |

FIGS. 8-11 illustrate results from the examples above.

FIG. 8: UV activation of Ink 6C with MB and H/I modifications.

FIG. 9: Air exposure of UV activated Ink 6C with MB and H/I modifications

FIG. 10: UV activation and air exposure (after 2 mins) of Ink 4 with RR and H/I modifications FIG. 11: UV activation and air exposure (after 15 mins) of Ink 4 with RR and H/I modifications Whereas particular embodiments of this invention have been described above for purposes of illustration, it will be evident to those skilled in the art that numerous variations of the details of the present invention may be made without departing from the invention.

Whereas particular embodiments of this invention have been described above for purposes of illustration, it will be evident to those skilled in the art that numerous variations of the details of the present invention may be made without departing from the invention as defined in the appended claims.

What is claimed is:

1. A damage indicating package comprising a first packaging layer and a second packaging layer attached to the first packaging layer thereby forming a product pocket having an interior volume between the first packaging layer and the second packaging layer structured and arranged to receive a product, wherein the first packaging layer comprises:
    an inner wrapper layer comprising a film having an interior surface exposed to the interior volume of the product pocket;
    an outer layer comprising a film at least partially covering the inner wrapper layer and the interior volume of the product pocket and forming a damage indicating material pocket between an exterior surface of the inner wrapper layer and an interior surface of the outer layer, wherein the damage indicating material pocket is evacuated or at least partially filled with an inert gas; and
    a damage indicating material in the damage indicating material pocket between the exterior surface of the inner wrapper layer and the interior surface of the outer wrapper layer.

2. The damage indicating package of claim 1, wherein the product is a condom.

3. The damage indicating package of claim 1, wherein the product is a food product or a pharmaceutical product.

4. The damage indicating package of claim 1, wherein the damage indicating material changes color when exposed to oxygen.

5. The damage indicating package of claim 1, wherein the damage indicating material comprises methylene blue.

6. The damage indicating package of claim 1, wherein the damage indicating material is applied to the interior surface of the outer layer.

7. The damage indicating package of claim 1, wherein the damage indicating material is applied to the exterior surface of the inner wrapper layer.

8. The damage indicating package of claim 1, wherein the outer layer is coextensive with the inner wrapper layer.

9. The damage indicating package of claim 1, wherein the damage indicating material is applied to the inner wrapper layer or the outer layer in the form of indicia.

10. The damage indicating package of claim 1, wherein the damage indicating material comprises an anti-counterfeiting taggant material.

11. The damage indicating package of claim 1, wherein the second packaging layer comprises:
    an inner wrapper layer comprising a film having an interior surface exposed to the interior volume of the product pocket;
    an outer layer comprising a film at least partially covering the inner wrapper layer and the interior volume of the product pocket and forming a damage indicating material pocket between an exterior surface of the inner wrapper layer and an interior surface of the outer layer, wherein the damage indicating material pocket is evacuated or at least partially filled with an inert gas; and
    a damage indicating material in the damage indicating material pocket between the exterior surface of the inner wrapper layer and the interior surface of the outer wrapper layer.

12. A packaged product comprising a first packaging layer and a second packaging layer attached to the first packaging layer thereby forming a product pocket having an interior volume between the first packaging layer and the second packaging layer with the packaged product contained within the product pocket, wherein the first packaging layer comprises:
    an inner wrapper layer comprising a film having an interior surface exposed to the interior volume of the product pocket;
    an outer layer comprising a film at least partially covering the inner wrapper layer and the interior volume of the product pocket and forming a damage indicating material pocket between an exterior surface of the inner wrapper layer and an interior surface of the outer layer, wherein the damage indicating material pocket is evacuated or at least partially filled with an inert gas; and a damage indicating material in the damage indicating material pocket between the exterior surface of the inner wrapper layer and the interior surface of the outer wrapper layer.

13. The packaged product of claim 12, wherein the product is a condom.

14. The packaged product of claim 12, wherein the product is a food product or a pharmaceutical product.

15. A method of making a damage indicating product package comprising applying a damage indicating material to a layer of wrapper material, and wrapping a product in the wrapper material to produce a packaged product as recited in claim 12.

16. A method of providing an indication that a product package has been damaged comprising wrapping the product with at least one layer having a damage indicating material applied thereto to produce a packaged product as recited in claim 12, wherein the damage indicating material changes appearance when exposed to oxygen upon damage of the product package.

17. The packaged product of claim 12, wherein the second packaging layer comprises:

an inner wrapper layer comprising a film having an interior surface exposed to the interior volume of the product pocket;

an outer layer comprising a film at least partially covering the inner wrapper layer and the interior volume of the product pocket and forming a damage indicating material pocket between an exterior surface of the inner wrapper layer and an interior surface of the outer layer, wherein the damage indicating material pocket is evacuated or at least partially filled with an inert gas; and a damage indicating material in the damage indicating material pocket between the exterior surface of the inner wrapper layer and the interior surface of the outer wrapper layer.

* * * * *